(12) United States Patent
Lee et al.

(10) Patent No.: US 11,364,158 B2
(45) Date of Patent: Jun. 21, 2022

(54) ABSORBENT ARTICLE WITH AN ABSORBENT SYSTEM HAVING AN OPENING

(71) Applicant: Kimberly-Clark Worldwide, Inc., Neenah, WI (US)

(72) Inventors: JuHyung Lee, Anyang-si (KR); HyungWoo Park, Suwon-si (KR); SungSu Kim, Yongin-si (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 842 days.

(21) Appl. No.: 16/310,926

(22) PCT Filed: Jun. 29, 2016

(86) PCT No.: PCT/US2016/040037
§ 371 (c)(1),
(2) Date: Dec. 18, 2018

(87) PCT Pub. No.: WO2018/004564
PCT Pub. Date: Jan. 4, 2018

(65) Prior Publication Data
US 2021/0220190 A1 Jul. 22, 2021

(51) Int. Cl.
*A61F 13/537* (2006.01)
*A61F 13/15* (2006.01)
*A61F 13/53* (2006.01)

(52) U.S. Cl.
CPC .. *A61F 13/53717* (2013.01); *A61F 13/53756* (2013.01); *A61F 2013/15406* (2013.01);
(Continued)

(58) Field of Classification Search
CPC ........ A61F 13/15; A61F 13/472; A61F 13/53; A61F 13/534; A61F 13/535;
(Continued)

(56) References Cited

U.S. PATENT DOCUMENTS 3,441,023 A  4/1969  Rijssenbeek et al.
3,889,679 A  6/1975  Taylor
(Continued)

FOREIGN PATENT DOCUMENTS

CN  201410036 Y  2/2010
CN  101868209 A  10/2010
(Continued)

*Primary Examiner* — Michele M Kidwell
(74) *Attorney, Agent, or Firm* — Kimberly-Clark Worldwide, Inc.

(57) ABSTRACT

An absorbent article can have a top sheet layer, a back sheet layer, and an absorbent system positioned between the top sheet layer and the back sheet layer. The absorbent system can have at least a fluid intake layer, an absorbent core, and a distribution layer. The fluid intake layer can define a fluid intake layer opening and the absorbent core can define an absorbent core opening. A void space is present between the top sheet layer and the distribution layer and the top sheet layer is maintained in a spaced apart relationship from the distribution layer.

12 Claims, 7 Drawing Sheets

(52) U.S. Cl.
CPC .............. *A61F 2013/15959* (2013.01); *A61F 2013/15967* (2013.01); *A61F 2013/530007* (2013.01); *A61F 2013/53782* (2013.01); *A61F 2013/53795* (2013.01)

(58) Field of Classification Search
CPC .......... A61F 13/53717; A61F 13/53747; A61F 13/53756; A61F 2013/15406; A61F 2013/15959; A61F 2013/15967; A61F 2013/530007; A61F 2013/53782; A61F 2013/53795; A61F 13/53713; A61F 2013/53445; A61F 2013/5355
See application file for complete search history.

(56) References Cited

U.S. PATENT DOCUMENTS

| | | | |
|---|---|---|---|
| 4,285,342 A | 8/1981 | Mesek | |
| 4,501,586 A | 2/1985 | Holtman | |
| 4,624,666 A | 11/1986 | DeRossett et al. | |
| 4,662,876 A | 5/1987 | Wiegner | |
| 4,731,065 A | 3/1988 | Yamada | |
| 4,892,534 A * | 1/1990 | Datta | A61F 13/51121 428/397 |
| 4,988,344 A | 1/1991 | Reising et al. | |
| 4,988,345 A | 1/1991 | Reising | |
| 5,062,840 A * | 11/1991 | Holt | A61F 13/495 604/385.19 |
| 5,176,672 A * | 1/1993 | Bruemmer | A61F 13/511 604/385.19 |
| 5,304,161 A | 4/1994 | Noel et al. | |
| 5,348,547 A | 9/1994 | Payne et al. | |
| H1377 H | 11/1994 | Perry | |
| 5,397,316 A | 3/1995 | LaVon et al. | |
| 5,415,640 A | 5/1995 | Kirby et al. | |
| 5,429,632 A | 7/1995 | Tanji et al. | |
| 5,439,458 A | 8/1995 | Noel et al. | |
| 5,533,991 A | 7/1996 | Kirby et al. | |
| 5,580,418 A | 12/1996 | Alikhan | |
| 5,662,633 A | 9/1997 | Doak et al. | |
| 5,669,798 A | 9/1997 | Koczab | |
| 5,755,710 A | 5/1998 | Menard | |
| 5,810,798 A | 9/1998 | Finch et al. | |
| 5,855,719 A | 1/1999 | Menard | |
| 5,961,505 A | 10/1999 | Coe et al. | |
| 5,990,375 A | 11/1999 | Lindquist et al. | |
| 6,117,523 A | 9/2000 | Sugahara | |
| 6,241,714 B1 | 6/2001 | Raidel et al. | |
| 6,436,080 B1 | 8/2002 | Carlucci et al. | |
| 6,461,339 B1 | 10/2002 | Sugahara | |
| 6,573,424 B1 | 6/2003 | Raidel et al. | |
| 6,685,688 B2 | 2/2004 | Mishima et al. | |
| 6,700,036 B2 | 3/2004 | Thomas et al. | |
| 6,911,574 B1 | 6/2005 | Mizutani | |
| 7,160,280 B2 * | 1/2007 | Bailey | A61F 13/495 604/348 |
| 7,285,178 B2 | 10/2007 | Mischler et al. | |
| 7,388,123 B2 | 6/2008 | Cowell et al. | |
| 7,429,689 B2 | 9/2008 | Chen et al. | |
| 7,442,188 B2 | 10/2008 | Franklin et al. | |
| 7,462,755 B2 | 12/2008 | Toro et al. | |
| 7,674,949 B2 | 3/2010 | Wahlstrom et al. | |
| 7,786,340 B2 | 8/2010 | Gagliardi et al. | |
| 7,824,385 B2 | 11/2010 | Ecker et al. | |
| 7,927,320 B2 | 4/2011 | Goldwasser et al. | |
| 7,976,523 B2 | 7/2011 | Suzuki et al. | |
| 8,187,242 B1 | 5/2012 | Raidel et al. | |
| 8,211,078 B2 | 7/2012 | Noel | |
| 8,317,768 B2 | 11/2012 | Larsson | |
| 8,915,898 B2 * | 12/2014 | Dieringer | A61F 13/51104 604/385.101 |
| 10,667,960 B2 * | 6/2020 | Kim | A61F 13/4751 |
| 10,758,427 B2 * | 9/2020 | Nakayama | A61F 13/49009 |
| 10,842,688 B2 * | 11/2020 | Cho | A61F 13/47218 |
| 2003/0233080 A1 | 12/2003 | Backman et al. | |
| 2006/0122572 A1 | 6/2006 | Suarez | |
| 2006/0148917 A1 | 7/2006 | Radwanski et al. | |
| 2007/0055210 A1 | 3/2007 | Kao | |
| 2007/0078422 A1 | 4/2007 | Glaug et al. | |
| 2010/0256586 A1 | 10/2010 | Bergström et al. | |
| 2011/0060303 A1 | 3/2011 | Bissah et al. | |
| 2011/0106036 A1 | 5/2011 | Ståhl et al. | |
| 2012/0220972 A1 * | 8/2012 | Kawamura | A61F 13/49001 604/383 |
| 2012/0277711 A1 | 11/2012 | Kim et al. | |
| 2014/0121621 A1 * | 5/2014 | Kirby | A61F 13/51104 604/374 |
| 2015/0068976 A1 | 3/2015 | Lemaire et al. | |
| 2015/0182387 A1 * | 7/2015 | Ferrer | A61L 15/225 604/366 |
| 2015/0245958 A1 | 9/2015 | Chmielewski et al. | |
| 2015/0313766 A1 * | 11/2015 | Miao | A61F 13/475 604/385.101 |
| 2017/0151104 A1 * | 6/2017 | Yu | A61F 13/53747 |

FOREIGN PATENT DOCUMENTS

| | | |
|---|---|---|
| CN | 101897638 A | 12/2010 |
| CN | 102573729 A | 7/2012 |
| CN | 105473113 A | 4/2016 |
| EP | 0619726 B2 | 6/2000 |
| EP | 1301156 B1 | 8/2006 |
| EP | 1842512 B1 | 9/2011 |
| EP | 1196122 B2 | 11/2011 |
| EP | 1842513 B1 | 9/2014 |
| GB | 1425179 A | 2/1976 |
| GB | 1595393 A | 8/1981 |
| GB | 2284767 A1 | 6/1995 |
| JP | 2004033236 A | 2/2004 |
| JP | 2012050499 A | 3/2012 |
| SE | 520706 C2 | 8/2003 |
| WO | 03086257 A1 | 10/2003 |
| WO | 13185800 A1 | 12/2013 |
| WO | 2016053230 A1 | 4/2016 |

\* cited by examiner

ABSORBENT ARTICLE WITH AN ABSORBENT SYSTEM HAVING AN OPENING

BACKGROUND

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

One problem with such conventional absorbent articles is that the body exudates are usually directed towards one portion of the absorbent article while the absorption capacity of the absorbent article is spread over a greater area. In a conventional absorbent article, such as one containing cellulosic material, when body exudates are absorbed by the cellulosic material, the capillary walls of the cellulosic material can collapse inward. This collapse can prevent the body exudates from being conducted downward and into the absorbent article and can substantially diminish the inherent resiliency of the cellulosic material. This can ultimately lead to early failure of the absorbent article as the body exudates to be absorbed cannot be efficiently spread throughout the absorbent article. If the body exudates to be absorbed cannot be efficiently spread through the absorbent article, they may run off the edge of the absorbent article causing leakage and staining.

A related problem is that after the capillaries of the cellulosic material collapse, body exudates which would normally be conducted downward into the absorbent article tends to remain at or near the top surface of the absorbent article. This can contribute to the body exudate failing to penetrate the topsheet layer of the absorbent article thereby providing the wearer of the absorbent article with a wet, uncomfortable body facing surface of the absorbent article.

As a result, there remains a need for an improved product, such as an absorbent article, that has an improved vertical wicking capability and an improved liquid distribution capability.

SUMMARY

In various embodiments, an absorbent article can have a longitudinal direction, a transverse direction, and a depth direction; a topsheet layer and a backsheet layer; and an absorbent system positioned between the topsheet layer and the backsheet layer, the absorbent system can have a fluid intake layer positioned below the topsheet layer in the depth direction of the absorbent article; an absorbent core positioned below the fluid intake layer in the depth direction of the absorbent article; and a distribution layer positioned below the absorbent core in the depth direction of the absorbent article and capable of distributing fluid in at least the longitudinal direction of the absorbent article; wherein the fluid intake layer defines a fluid intake layer opening having a first longitudinal length and a first transverse width and the absorbent core defines an absorbent core opening having a second longitudinal length and a second transverse width wherein the second longitudinal length and the second transverse width of the absorbent core opening is smaller than the first longitudinal length and first transverse width of the fluid intake layer opening and wherein a spatial gap exists between the topsheet layer and the distribution layer.

In various embodiments, the distribution layer is a hydroentangled web. In various embodiments, the hydroentangled web comprises a spunbond material and a pulp material. In various embodiments, the spunbond material is present in an amount from about 10-25% of the hydroentangled web and the pulp material is present in an amount from about 75-90% of the hydroentangled web.

In various embodiments, the distribution layer is a meltblown microfiber web.

In various embodiments, the distribution layer comprises a hydrophilic material. In various embodiments, the distribution layer has a density greater than about 0.1 grams. In various embodiments, the distribution layer has a basis weight from about 10 gsm to about 300 gsm. In various embodiments, distribution layer has a longitudinal length from about 80 mm to about 190 mm.

In various embodiments, the distribution layer has a transverse width from about 20 mm to about 60 mm.

In various embodiments, the fluid intake layer opening has a longitudinal length from about 15 mm to about 150 mm. In various embodiments, the fluid intake layer opening has a transverse width from about 10 mm to about 80 mm.

In various embodiments, a height of the spatial gap from the topsheet layer to the distribution layer is from about 1 mm to about 8 mm.

In various embodiments, the absorbent article further has a shield layer. In various embodiments, the shield layer comprises an aperture film material.

In various embodiments, the absorbent article further has a surge layer.

DETAILED DESCRIPTION

Figure 1:
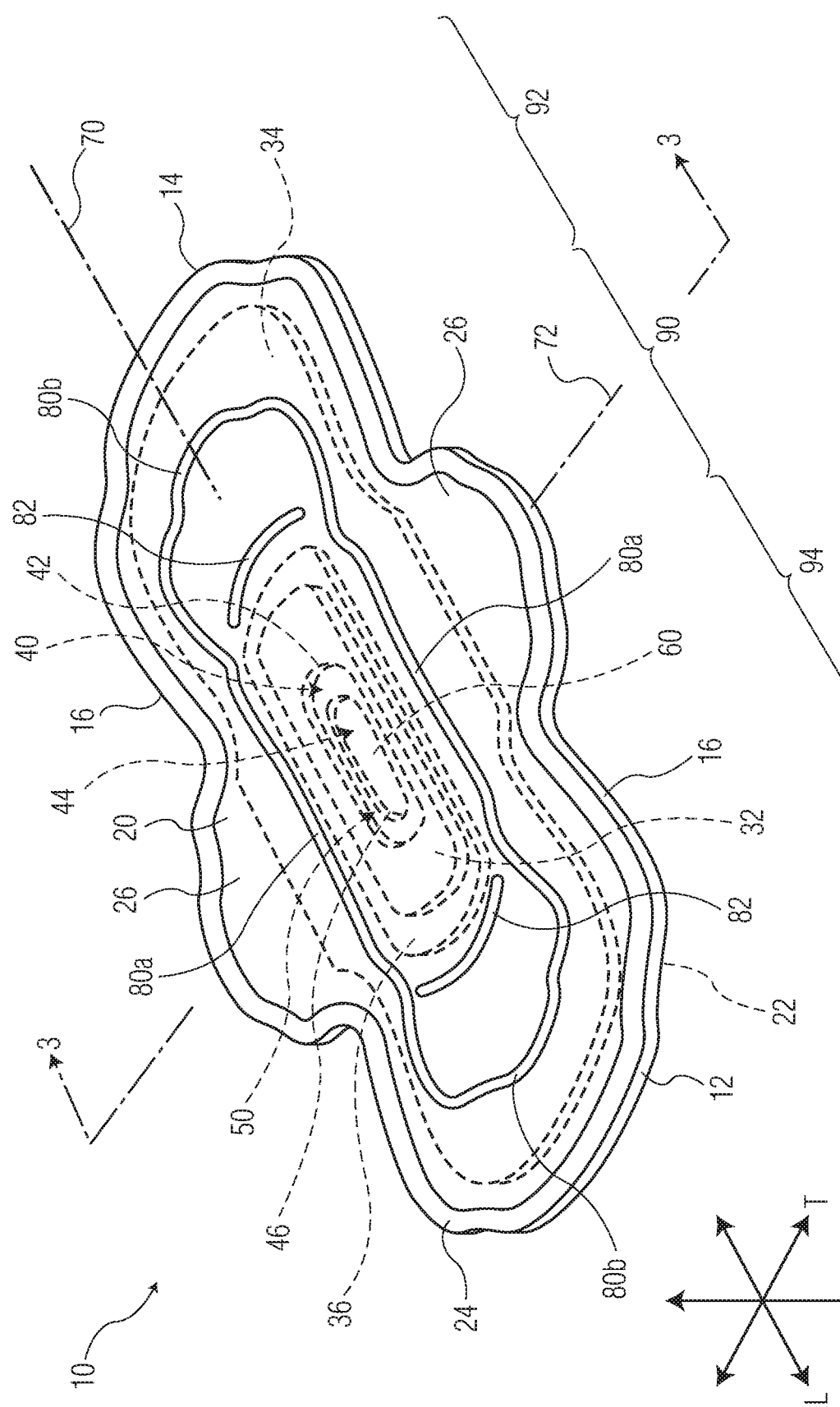
FIG. 1 is a perspective view of an embodiment of an absorbent article.

The present disclosure is generally directed towards an absorbent article which can have an improved vertical wicking capability and an improved liquid distribution capability. An absorbent article can have a longitudinal direction, a transverse direction, and a depth direction. The absorbent article can have a topsheet layer, a backsheet layer, and an absorbent system positioned between the topsheet layer and the backsheet layer. The absorbent system can have at least a fluid intake layer, an absorbent core, and a distribution layer. The fluid intake layer can be positioned below the topsheet layer in the depth direction of the absorbent article. The absorbent core can be positioned below the fluid intake layer in the depth direction of the absorbent article. The distribution layer can be positioned below the absorbent core in the depth direction of the absorbent article. The distribution layer can be capable of distributing fluid in at least the longitudinal direction of the absorbent article. The fluid intake layer can define a fluid intake layer opening and the absorbent core can define an absorbent core opening. The absorbent core opening can have a size dimension smaller than the size dimension of the fluid intake layer opening. As the absorbent core is positioned below the fluid intake layer, the absorbent core opening can underlay the fluid intake layer opening. The combination of such positioning and size dimensions of the absorbent core opening and fluid intake layer opening can result in an absorbent system opening wherein the transverse width and longitudinal length dimensions of the absorbent system opening decreases when measured in the depth direction (Z) of the absorbent article from the topsheet layer to the body facing surface of the distribution layer. The transverse width and longitudinal length dimensions of the absorbent system opening closer to the topsheet layer will be greater than the transverse width and longitudinal length dimensions of the absorbent system opening closer to the distribution layer.

The openings in each of the fluid intake layer and the absorbent core can result in a reduction of the overall absorption capacity of the absorbent article in a localized region of the absorbent article. While the overall absorption capacity in a localized region has been reduced, the opening in each of the fluid intake layer and absorbent core can create a void space which can expose a portion of the distribution layer such that the exposed portion of the distribution layer of the absorbent system can be visible to the wearer through the openings of each of the fluid intake layer and the absorbent core. Each opening can allow for body exudates to pass directly to the distribution layer of the absorbent article. Acquisition of the body exudates by the distribution layer can allow for rapid acquisition of the body exudates into the absorbent article. The distribution layer can then distribute the body exudates in at least the longitudinal direction of the absorbent article and in a direction towards the absorbent core of the absorbent system. As the absorbent core is positioned above the distribution layer, the absorbent article can, therefore, absorb body exudates in a direction opposite the direction of gravity (bottom layer to top layer direction). At least a portion of the topsheet layer can be maintained in a spaced apart relationship from the distribution layer due to the void space created by the openings in each of the fluid intake layer and the absorbent core.

Definitions

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea"

arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article

The present disclosure is generally directed towards an absorbent article which can have an improved vertical wicking capability and an improved liquid distribution capability. An absorbent article can have a longitudinal direction, a transverse direction, and a depth direction. The absorbent article can have a topsheet layer, a backsheet layer, and an absorbent system positioned between the topsheet layer and the backsheet layer. The absorbent system can have at least a fluid intake layer, an absorbent core, and a distribution layer. The fluid intake layer can be positioned below the topsheet layer in the depth direction of the absorbent article. The absorbent core can be positioned below the fluid intake layer in the depth direction of the absorbent article. The distribution layer can be positioned below the absorbent core in the depth direction of the absorbent article. The distribution layer can be capable of distributing fluid in at least the longitudinal direction of the absorbent article. The fluid intake layer can define a fluid intake layer opening and the absorbent core can define an absorbent core opening. The absorbent core opening can have a size dimension smaller than the size dimension of the fluid intake layer opening. As the absorbent core is positioned below the fluid intake layer, the absorbent core opening can underlay the fluid intake layer opening. The combination of such positioning and size dimensions of the absorbent core opening and fluid intake layer opening can result in an absorbent system opening wherein the transverse width and longitudinal length dimensions of the absorbent system opening decreases when measured in the depth direction (Z) of the absorbent article from the topsheet layer to the body facing surface of the distribution layer. The transverse width and longitudinal length dimensions of the absorbent system opening closer to the topsheet layer will be greater than the transverse width and longitudinal length dimensions of the absorbent system opening closer to the distribution layer.

The openings in each of the fluid intake layer and the absorbent core can result in a reduction of the overall absorption capacity of the absorbent article in a localized region of the absorbent article. While the overall absorption capacity in a localized region has been reduced, the opening in each of the fluid intake layer and absorbent core can create a void space which can expose a portion of the distribution layer such that the exposed portion of the distribution layer of the absorbent system can be visible to the wearer through the openings of each of the fluid intake layer and the absorbent core. Each opening can allow for body exudates to pass directly to the distribution layer of the absorbent article. Acquisition of the body exudates by the distribution layer can allow for rapid acquisition of the body exudates into the absorbent article. The distribution layer can then distribute the body exudates in at least the longitudinal direction of the absorbent article and in a direction towards the absorbent core of the absorbent system. As the absorbent core is positioned above the distribution layer, the absorbent article can, therefore, absorb body exudates in a direction opposite the direction of gravity (bottom layer to top layer direction). At least a portion of the topsheet layer can be maintained in a spaced apart relationship from the distribution layer due to the void space created by the openings in each of the fluid intake layer and the absorbent core.

Figure 2:
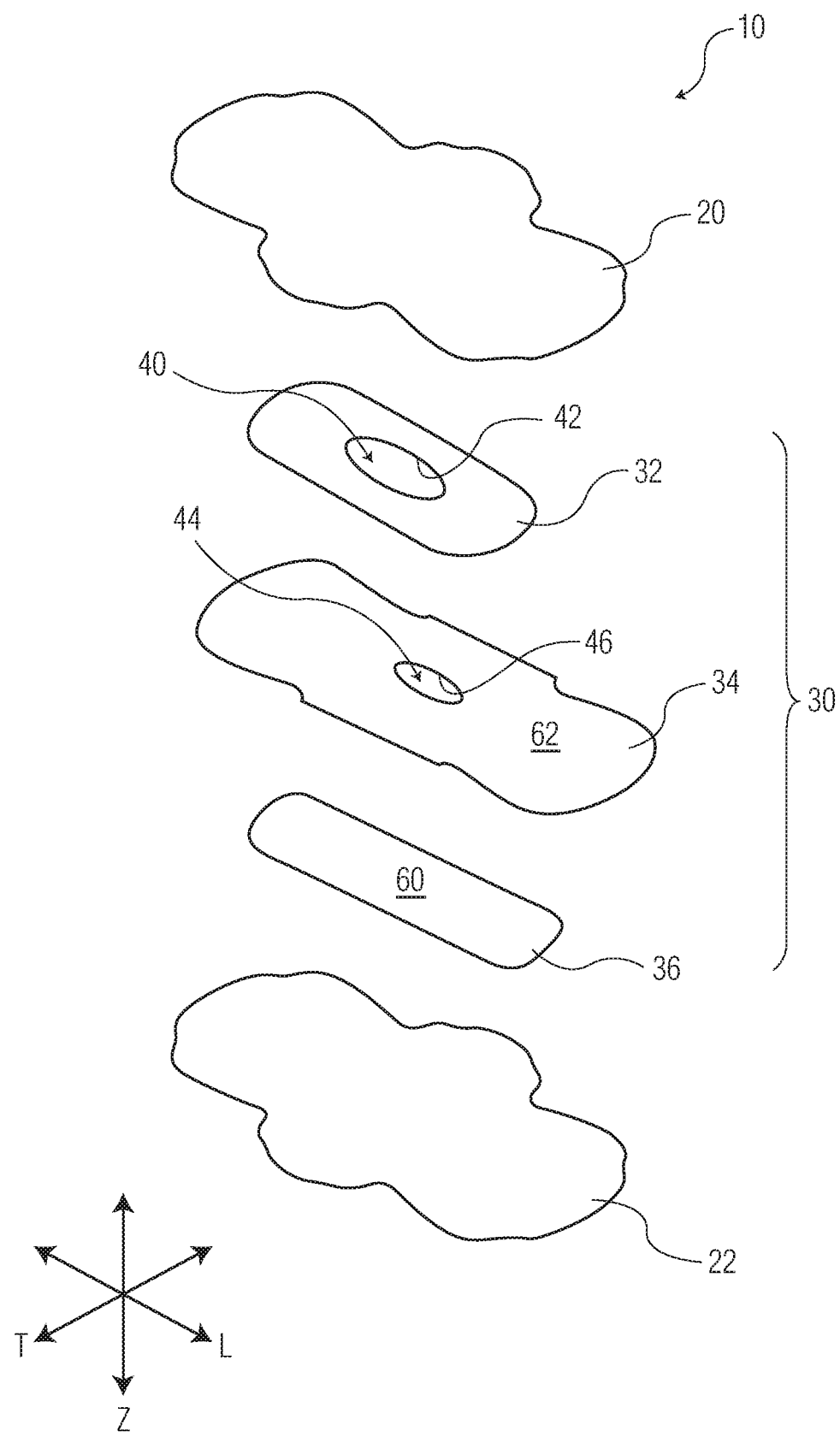
FIG. 2 is an exploded perspective view of the absorbent article of FIG. 1.
Figure 3:
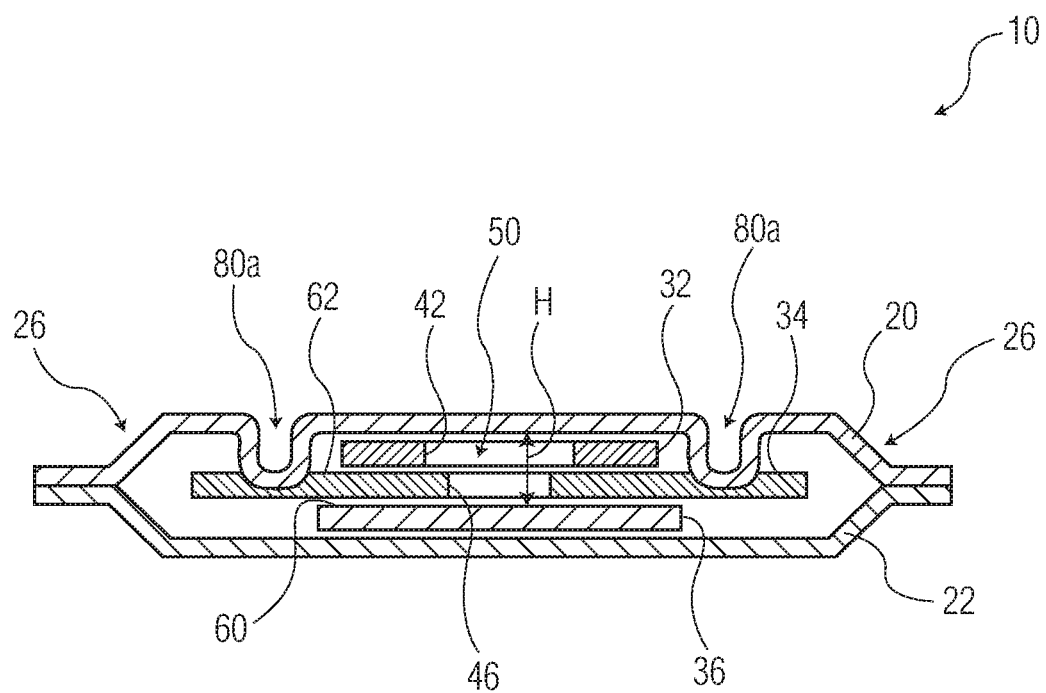
FIG. 3 is a cross-sectional view of the absorbent article of FIG. 1 taken along line 3-3.

Referring to FIGS. 1-3, FIG. 1 provides an illustration of a perspective view of an exemplary absorbent article 10, FIG. 2 provides an illustration of an exploded perspective view of the absorbent article 10 of FIG. 1, and FIG. 3 provides an illustration of a cross-sectional view of the absorbent article 10 of FIG. 1 taken along line 3-3. The absorbent article 10 can have a longitudinal direction (L), a transverse direction (T), and a depth direction (Z). The absorbent article 10 can have a first transverse direction end edge 12, a second transverse direction end edge 14 opposite the first transverse direction end edge 12, and a pair of opposing longitudinal direction side edges 16. In various embodiments, the absorbent article 10 can take on various geometries but will generally have a pair of opposing longitudinal direction side edges 16 and a pair of opposing transverse direction end edges 12 and 14. The absorbent article 10 can have a wearer facing, liquid permeable topsheet layer 20 and a garment facing, liquid impermeable backsheet layer 22. An absorbent system 30 can be positioned between the topsheet layer 20 and the backsheet layer 22. The absorbent system 30 can include a fluid intake layer 32, an absorbent core 34, and a distribution layer 36. The fluid intake layer 32 can define a fluid intake layer opening 40 and the absorbent core 34 can define an absorbent core opening 44. The fluid intake layer opening 40 and the absorbent core opening 44 together can define an absorbent system opening 50.

The topsheet layer 20 and the backsheet layer 22 can both extend beyond the outermost peripheral edges of the absorbent system 30 and can be peripherally bonded together, either entirely or partially, using known bonding techniques to form a sealed peripheral region 24. For example, the topsheet layer 20 and the backsheet layer 22 can be bonded together by adhesive bonding, ultrasonic bonding, or any other suitable bonding method known in the art.

In various embodiments, the absorbent article 10 can have a pair of wings 26 extending outwardly, in the transverse direction T, from the absorbent article 10. The wings 26 can drape over the edges of the wearer's undergarment so that the wings 26 are disposed between the edges of the wearer's undergarment and her thighs. The wings 26 can serve at least two purposes. First, the wings 26 can prevent soiling of the wearer's undergarment by forming a barrier along the edges of the undergarment. Second, the wings 26 can be provided with an attachment aid (not shown), such as, for example, a garment attachment adhesive or a hook, to keep the absorbent article 10 securely and properly positioned in the undergarment. The wings 26 can wrap around the crotch region of the wearer's undergarment to aid in securing the absorbent article 10 to the wearer's undergarment when in use. Each wing 26 can fold under the crotch region of the wearer's undergarment and the attachment aid can either form a secure attachment to the opposite wing 26 or directly to the surface of the wearer's undergarment. In various embodiments, the wings 26 can be an extension of materials forming the topsheet layer 20 and/or the backsheet layer 22, such that the wings 26 can be of a unitary construction with the absorbent article 10. In various embodiments, the wings 26 can be constructed of materials similar to the topsheet layer 20, the backsheet layer 22 or combinations of these materials. In various embodiments, the wings 26 can be separate elements bonded to the main body of the absorbent article 10. It is to be understood that the wings 26 are optional and, in various embodiments, an absorbent article 10 can be configured without wings 26.

Each of these components of the absorbent article 10, as well as additional components, will be described in more detail herein.

Topsheet Layer

The topsheet layer 20 defines a wearer facing surface of the absorbent article 10 that may directly contact the body of the wearer and is liquid permeable to receive body exudates. The topsheet layer 20 is desirably provided for comfort and conformability and functions to direct body exudates away from the body of the wearer, through its own structure, and towards the absorbent system 30. The topsheet layer 20 desirably retains little to no liquid in its structure, so that it provides a relatively comfortable and non-irritating surface next to the skin of the wearer of the absorbent article 10.

The topsheet layer 20 can be a single layer of material, or alternatively, can be multiple layers that have been laminated together. The topsheet layer 20 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 20.

In various embodiments, the topsheet layer 20 can be constructed from various nonwoven webs such as meltblown webs, spunbond webs, hydroentangled spunlace webs, or through air bonded carded webs. Examples of suitable topsheet layer 20 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 20 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 20, each of which is hereby incorporated by reference thereto in its entirety. Additional topsheet layer 20 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the topsheet layer 20 may contain a plurality of apertures (not shown) formed therethrough to permit body exudates to pass more readily into the absorbent system 30. The apertures may be randomly or uniformly arranged throughout the topsheet layer 20. The size, shape, diameter, and number of apertures may be varied to suit an absorbent article's 10 particular needs.

In various embodiments, the topsheet layer 20 can have a basis weight ranging from about 5, 10, 15, 20 or 25 gsm to about 50, 100, 120, 125 or 150 gsm. For example, in an embodiment, a topsheet layer 20 can be constructed from a through air bonded carded web having a basis weight ranging from about 15 gsm to about 100 gsm. In another example, a topsheet layer 20 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others.

In various embodiments, the topsheet layer 20 can be at least partially hydrophilic. In various embodiments, a portion of the topsheet layer 20 can be hydrophilic and a portion of the topsheet layer 20 can be hydrophobic. In various embodiments, the portions of the topsheet layer 20 which can be hydrophobic can be either an inherently hydrophobic material or can be a material treated with a hydrophobic coating.

Figure 6:
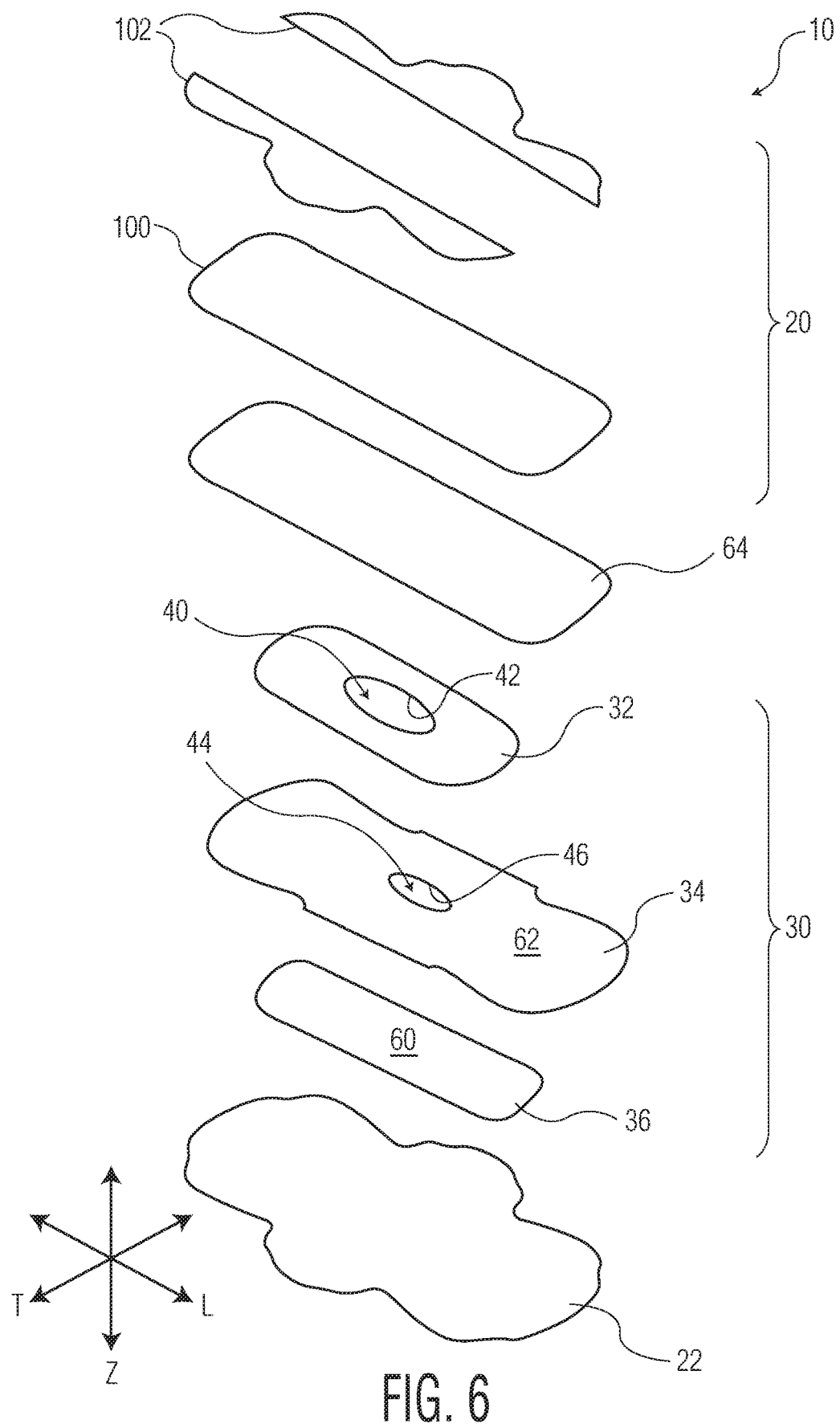
FIG. 6 is an exploded perspective view of an embodiment of an absorbent article.

In various embodiments, the topsheet layer 20 can be a multicomponent topsheet layer 20 such as by having two or more different nonwoven or film materials, with the different materials placed in separate locations in the transverse direction T of the absorbent article 10. For example, referring to FIGS. 6 and 7, the topsheet layer 20 can be a two layer or multicomponent material having a central portion 100 positioned along and straddling a longitudinal centerline 70 (such as illustrated in FIG. 1) of the absorbent article 10, with lateral side portions 102 flanking and bonded to each side edge of the central portion 100. The central portion 100 can be constructed from a first material and the side portions 102 can be constructed from a material which can be the same as or different from the material of the central portion 100. In such embodiments, the central portion 100 may be at least partially hydrophilic and the side portions may be inherently hydrophobic or may be treated with a hydrophobic coating. Examples of constructions of multi-component topsheet layers 20 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

Figure 7:
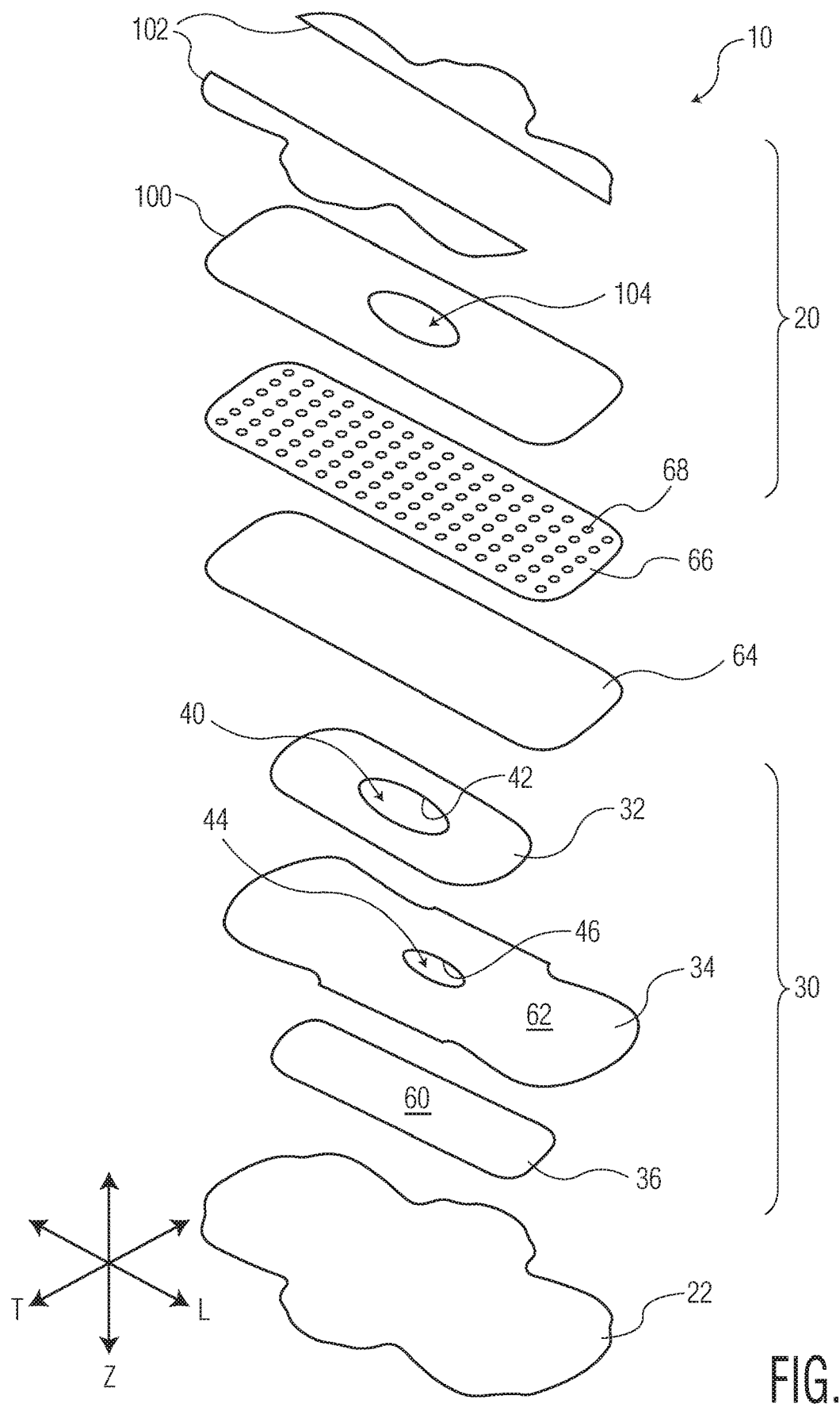
FIG. 7 is an exploded perspective view of an embodiment of an absorbent article.

In various embodiments, a central portion 100 of a topsheet layer 20 can be positioned symmetrically about the absorbent article 10 longitudinal centerline 70. Such central longitudinally directed central portion 100 can be a through air bonded carded web ("TABCW") having a basis weight between about 15 and about 100 gsm. Previously described nonwoven, woven, and apertured film topsheet layer materials may also be used as the central portion 100 of a topsheet layer 20. In various embodiments, the central portion 100 can be constructed from a TABCW material having a basis weight from about 20 to about 50 gsm such as is available from Xiamen Yanjan Industry, Beijing, DaYuan Nonwoven Fabrics, and others. Alternatively, apertured films, such as those available from such film suppliers as Texol, Italy and Tredegar, U.S.A. may be utilized. Referring to FIG. 7, in various embodiments it may be desirable to include an opening 104 in the central portion 100. Different nonwoven, woven, or film sheet materials may be utilized as the side portions 102 of the topsheet layer 20. The selection of such topsheet layer 20 materials can vary based upon the overall desired attributes of the topsheet layer 20. For example, it may be desired to have a hydrophilic material in the central portion 100 and hydrophobic-barrier type materials in the side portions 102 to prevent leakage and increase a sense of dryness in the area of the side portions 102. Such side portions 102 can be adhesively, thermally, ultrasonically, or otherwise bonded to the central portion 100 along or adjacent the longitudinally directed side edges of the central portion 100. Traditional absorbent article construction adhesive may be used to bond the side portions 102 to the central portion 100. Either of the central portion 100 and/or the side portions 102 may be treated with surfactants and/or skin-health benefit agents, as are well known in the art.

Such longitudinally directed side portions 102 can be of a single or multi-layered construction. In various embodiments, the side portions 102 can be adhesively or otherwise bonded laminates. In various embodiments, the side portions 102 can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 20 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 20. The film layer may also serve as a barrier layer to prevent rewet of the topsheet layer 20 as well as to prevent the flow of fluid off the side edges of the absorbent article 10. In various embodiments, the side portions 102 can be laminates such as a spunbond-meltblown-meltblown-spunbond layer ("SMMS") laminate, spunbond-film laminate, or alternatively, other nonwoven laminate combinations.

Absorbent System

The absorbent system 30 can include at least a fluid intake layer 32, an absorbent core 34, and a distribution layer 36. The fluid intake layer 32 can define a fluid intake layer opening 40 and the absorbent core 34 can define an absorbent core opening 44. The fluid intake layer opening 40 and the absorbent core opening 44 can create a void space within the absorbent system 30. The openings, 40 and 44, in the fluid intake layer 32 and absorbent core 34, respectively, can expose a portion of the distribution layer 36. The exposed portion of the distribution layer 36 can be visible to the wearer of the absorbent article 10 through the openings, 40 and 44, in the fluid intake layer 32 and absorbent core 34, respectively. Together, the openings 40 and 44, in the fluid intake layer 32 and absorbent core 34, respectively, can define an absorbent system opening 50. The absorbent system opening 50 can allow body exudates to pass through the topsheet layer 20 and directly to the distribution layer 36 where the body exudates can be quickly absorbed by the distribution layer 36. Thus, it can be possible to minimize or prevent body exudates from leaking or oozing outwardly from the absorbent article 10 prior to the body exudates being ultimately absorbed into the absorbent system 30.

The absorbent system opening 50 can be formed by incorporating an opening into each of the fluid intake layer 32 and the absorbent core 34 and overlaying such openings. In embodiments in which the absorbent core 34 is formed of a single layer, the opening in the absorbent core 34 can be incorporated into the single layer of material of the absorbent core 34. In embodiments in which the absorbent core 34 is formed of multiple layers of material, an opening can be incorporated into each layer of material forming the absorbent core 34.

The absorbent system opening 50 can be bounded by the perimeters forming each opening in each of the fluid intake layer 32 and the absorbent core 34. For example, as illustrated in FIGS. 1-3, the absorbent system opening 50 can be bounded by perimeter 42 of the fluid intake layer opening 40 and by perimeter 46 of the absorbent core opening 44. The perimeters, 42 and 46, can form the inner border or inner edge of each of the fluid intake layer 32 and absorbent core 34, respectively, and the outer border of the absorbent system opening 50. It can be through the absorbent system opening 50 that at least a portion of the distribution layer 36 can be exposed and visible due to the void space created in the absorbent system 30 at the absorbent system opening 50. The absorbent system opening 50 can be any suitable shape, such as ovular, circular, rectangular, square, triangular, etc. The shape of the absorbent system opening 50 can be provided by the shapes of the perimeters, 42 and 46, of the openings, 40 and 44, in the fluid intake layer 32 and absorbent core 34, respectively.

The topsheet layer 20 can be in a spaced apart relationship from the distribution layer 36 in the region of the absorbent system opening 50 such that a spatial gap exists between the topsheet layer 20 and the distribution layer 36. In remaining spaced apart from the distribution layer 36, the tosphsheet layer 20 does not contact the distribution layer 36 and the spatial gap defines a void space between the topsheet layer 20 and the distribution layer 36. In other words, the spatial gap is the gap between the layers of the absorbent article 10, in the depth direction (Z) of the absorbent article 10, in which a void space is present, wherein the void space is not the result of normal interstitial spaces between immediately adjacent layers and is not the result where construction adhesive between immediately adjacent layers is absent. Such spatial gap is instead formed along a limited region of adjacent layers in which such regions are not in physical contact with one another only at such select regions and are separated by empty space, the void space, having a vertical distance along the depth direction (Z) of the absorbent article 10. The absorbent system opening 50, and, therefore, the void space, in the absorbent system 30, created by the incorporation of the openings, 40 and 44, into each of the fluid intake layers 32 and absorbent core 34, respectively, can extend in the depth direction (Z) of the absorbent article 10 from the topsheet layer 20 to the body facing surface 60 of the distribution layer 36. The height H, in the depth (Z) direction, of the absorbent system opening 50 and, therefore, the void space, as measured from the topsheet layer 20 to the body facing surface 60 of the distribution layer 36 can be from about 1, 1.5, 2, 2.5, 3, 3.5 or 4 mm to about 4.5, 5, 5.5, 6, 6.5, 7, 7.5 or 8 mm. In various embodiments, the height H, in the depth direction (Z), of the absorbent system opening 50 and, therefore, the void space as measured from the topsheet layer 20 to the body facing surface 60 of the distribution layer 36 can be from about 1.5 or 2 mm to about 2.5, 3, 3.5, or 4 mm.

The absorbent system opening 50 can be located at various positions along the longitudinal and transverse directions of the absorbent article 10 depending upon the primary location of body exudate intake or the purpose for which the absorbent article 10 is being used. For example, in various embodiments, the absorbent system opening 50 can be positioned so that it is in substantial alignment with the longitudinal centerline 70 and the transverse centerline 72 of the absorbent article 10. It should be understood that the longitudinal centerline 70 is disposed at a location that is equidistant from the longitudinal direction side edges 16 and runs the length of the absorbent article 10 in the longitudinal direction, while the transverse centerline 72 is disposed at a location that is equidistant from the first transverse direction end edge 12 and the second transverse direction end edge 14 and runs along the width of the absorbent article 10 in the transverse direction. This allows the absorbent system opening 50 to be centrally disposed so that it can be positioned below the main point of body exudate discharge and so that it can act as the primary body exudate receiving area for the absorbent article 10.

However, centralized positioning of the absorbent system opening 50 is not required, and in various embodiments, depending on the primary location where body exudate intake might occur, the absorbent system opening 50 of the absorbent article 10 may be substantially aligned with the longitudinal centerline 70 only. Thus, in various embodiments, the absorbent system opening 50 of the absorbent article 10 may be shifted in the longitudinal direction towards either of the transverse direction end edges, 12 or 14, of the absorbent article 10, so that the absorbent system opening 50 of the absorbent article 10 is not in substantial alignment with the transverse centerline 72.

The absorbent system opening 50 can have a first longitudinal length and a first transverse width as well as a second longitudinal length and a second transverse width. As described herein, the fluid intake layer 32 can define a fluid intake layer opening 40 and the absorbent core 34 can define an absorbent core opening 44. The first longitudinal length and the first transverse width of the absorbent system opening 50 can be equal to the longitudinal length and the transverse width, respectively, of the fluid intake layer opening 40. The second longitudinal length and the second transverse width of the absorbent system opening 50 can be equal to the longitudinal length and the transverse width, respectively, of the absorbent core opening 44. The absorbent system opening 50 can have a first longitudinal length from about 15, 20, 30 or 50 mm to about 60, 75, 100 or 150 mm and can have a first transverse width from about 10, 15, 20 or 30 mm to about 40, 50, 60 or 80 mm. The absorbent system opening 50 can have a first longitudinal length that is from about 15, 20 or 25% to about 70, 75, or 80% of the overall longitudinal length of the absorbent article 10 in the longitudinal direction.

The absorbent system opening 50 can have a first transverse width that can be from about 20, 25 or 30% to about 70, 75 or 80% of the overall width of the absorbent article 10 in the transverse direction. The absorbent system opening 50 can have a height H, in the depth (Z) direction of the absorbent article 10, measured from the topsheet layer 20 to the body facing surface 60 of the distribution layer 36, of from about 1, 1.5, 2, 2.5, 3, 3.5 or 4 mm to about 4.5, 5, 5.5, 6, 6.5, 7, 7.5 or 8 mm. The absorbent system opening 50 can have a height H, in the depth (Z) direction of the absorbent article 10, measured from the topsheet layer 20 to the body facing surface 60 of the distribution layer 36, from about 1.5 or 2 mm to about 2.5, 3, 3.5, or 4 mm. The absorbent system opening 50 can serve to funnel and direct body exudates from the topsheet layer 20 towards the distribution layer 36 of the absorbent article 10 in the depth (Z) direction. The absorbent system opening 50 can also form a cup or well-like structure for holding body exudates and preventing leakage of the body exudates away from a central region 90 of the absorbent article 10 and towards the edges of the absorbent article 10.

In various embodiments, the absorbent system opening 50 can be elongate and can be oriented in the longitudinal direction of the absorbent article 10. In such embodiments, when the absorbent system opening 50 is elongate and oriented in the longitudinal direction of the absorbent article 10, the body exudates may tend to be absorbed and spread in the longitudinal direction of the absorbent article 10 rather than in the transverse direction of the absorbent article 10. Accordingly, it can be possible to minimize or prevent the body exudates from heavily spreading in the transverse direction of the absorbent article 10 and thereby leaking out of the absorbent article 10.

Fluid Intake Layer

In various embodiments, the absorbent article 10 can include a liquid permeable fluid intake layer 32 positioned between the topsheet layer 20 and the absorbent core 34. Such a fluid intake layer 32 can be made of a material that can be capable of rapidly transferring, in the Z-direction, body exudates that are delivered to the topsheet layer 20. The fluid intake layer 32 can generally have any shape and/or size desired. In an embodiment, the fluid intake layer 32 can have a curved rectangular shape, with a length equal to or less than the overall length of the absorbent article 10, and a width less than the width of the absorbent article 10. For example, the fluid intake layer 32 can have a length of between about 20, 40 or 60 mm to about 150, 150, 175, 200 or 300 mm and a width of between about 10, 15 or 20 mm to about 60, 80 or 100 mm may be utilized. The fluid intake layer 32 can have a thickness in the depth direction from about 0.5 mm to about 3 mm. Any of a variety of different materials can be capable of being used for the fluid intake layer 32 to accomplish the above-mentioned functions. The material may be synthetic, cellulosic, or a combination of synthetic and cellulosic materials. The fluid intake layer 32 can be constructed from any woven or nonwoven material. For example, the fluid intake layer 32 can be constructed as an airlaid or TABCW material. For example, airlaid cellulosic tissues may be suitable for use in the fluid intake layer 32. The airlaid cellulosic tissue may have a basis weight ranging from about 10 or 100 gsm to about 250 or 300 gsm. The airlaid cellulosic tissue can be formed from hardwood and/or softwood fibers. An airlaid cellulosic tissue can have a fine pore structure and can provide an excellent wicking capacity, especially for menses.

Additionally, to further enhance the ability of the absorbent article 10 to transfer body exudates in the depth (Z) direction from the topsheet layer 20 toward any lower layers in the absorbent article 10 as well as to enhance the ability of the fluid intake layer 32 to conform to the wearer's body based on its ability to bend, the fluid intake layer 32 can have a fluid intake layer opening 40 which can be any suitable shape, such as ovular, circular, rectangular, square, triangular, etc. In various embodiments, the fluid intake layer opening 40 can be elongate and can be oriented in the longitudinal direction of the absorbent article 10. The fluid intake layer opening 40 can be bounded by a perimeter 42 which can form an inner border or inner edge of the fluid intake layer 32, leaving the fluid intake layer opening 40 through which at least a portion of the distribution layer 36 can be exposed and visible due to the lack of presence of the material, i.e., a void space, of the fluid intake layer 32 at the fluid intake layer opening 40.

The fluid intake layer opening 40 can be located at various positions along the longitudinal and transverse directions of the fluid intake layer 32 depending upon the primary location of body exudate intake or the purpose for which the absorbent article 10 is being used. For example, in various embodiments, the fluid intake layer 32 and the fluid intake layer opening 40 can be positioned so that it is in substantial alignment with the longitudinal centerline 70 and the transverse centerline 72 of the absorbent article 10. This allows the fluid intake layer opening 40 to be centrally disposed so that it can be positioned below the main point of body exudate discharge and so that it can act as the primary body exudate receiving area for the absorbent article 10.

However, centralized positioning of the fluid intake layer 32 and the fluid intake layer opening 40 is not required, and in various embodiments, depending on the primary location where body exudate intake might occur, the fluid intake layer 32 and the fluid intake layer opening 40 may be substantially aligned with the longitudinal centerline 70 only. Thus, in various embodiments, the fluid intake layer 32 and the fluid intake layer opening 40 may be shifted in the longitudinal direction towards either transverse direction end edge, 12 or 14, of the absorbent article 10, so that the fluid intake layer opening 40 is not in substantial alignment with the transverse centerline 72.

The fluid intake layer opening 40 can have a longitudinal length from about 15, 20, 30 or 50 mm to about 60, 75, 100 or 150 mm and can have a transverse width from about 10, 15, 20 or 30 mm to about 40, 60 or 80 mm. The fluid intake layer opening 40 can be defined by the perimeter 42 and can have a longitudinal length that is from about 15, 20 or 25% to about 70, 75, or 80% of the overall longitudinal length of the fluid intake layer 32 in the longitudinal direction. The fluid intake layer opening 40 can be defined by the perimeter 42 and can have a transverse width that can be from about 20, 25 or 30% to about 70, 75 or 80% of the overall width of the fluid intake layer 32 in the transverse direction. The fluid intake layer opening 40 can serve to funnel and direct body exudates from the topsheet layer 20 and towards lower layers of the absorbent article 10 in the depth (Z) direction. The fluid intake layer opening 40 can also form a cup or well-like structure for holding body exudates and preventing its leakage away from a central region 90 of the absorbent article 10 and towards the edges of the absorbent article 10.

Absorbent Core

An absorbent core 34 can be positioned between the topsheet layer 20 and the backsheet layer 22. The absorbent core 34 can be positioned beneath the fluid intake layer 32 in the depth direction of the absorbent article 10. The absorbent core 34 can generally be any single layer structure or combination of layer components, which can demonstrate some level of compressibility, conformability, be non-irritating to a wearer's skin, and capable of absorbing and retaining liquids and other body exudates. Additionally, the absorbent core 34 can provide additional capacity to absorb and retain body exudates such as menses. In various embodiments, the absorbent core 34 can be formed from a variety of different materials and can contain any number of desired layers. For example, the absorbent core 34 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 34 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly (vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 34 in any amount as desired.

Regardless of the combination of absorbent materials used in the absorbent core 34, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 34 can vary as desired and can comprise any one of various shapes including, but not limited to, triangular, rectangular, dog-bone and elliptical shapes. In various embodiments, the absorbent core 34 can have a shape that generally corresponds with the overall shape of the absorbent article 10. The dimensions of the absorbent core 34 can be substantially similar to those of the absorbent article 10, however, it will be appreciated that the dimensions of the absorbent core 34 while similar, will often be less than those of the overall absorbent article 10, in order to be adequately contained therein.

By way of example, suitable materials and/or structures for the absorbent core 34 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 34 can be a single layer structure and can include, for example, a matrix of cellulosic fluff and superabsorbent material. In various embodiments, an absorbent core 34 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 34 may be constructed of an airlaid material and the garment facing layer of the absorbent core 34 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Additionally, to further enhance the ability of the absorbent article 10 to transfer body exudates in the depth (Z) direction from the topsheet layer 20 toward any lower layers in the absorbent article 10 as well as to enhance the ability of the absorbent core 34 to conform to the wearer's body based on its ability to bend, the absorbent core 34 can have an absorbent core opening 44 which can be any suitable shape, such as ovular, circular, rectangular, square, triangular, etc. In various embodiments in which the absorbent core 34 comprises a single layer of material, the absorbent core opening 44 can exist in the single layer composing the absorbent core 34. In various embodiments in which the absorbent core 34 is formed of two layers, such as a body facing layer and a garment facing layer, the absorbent core 34 can have an opening in the body facing layer and in the garment facing layer 38. In various embodiments, the absorbent core opening 44 can be elongate and can be oriented in the longitudinal direction of the absorbent article 10. The absorbent core opening 44 can be bounded by a perimeter 46 which can form an inner border or inner edge of the absorbent core 34, leaving the absorbent core opening 44 through which at least a portion of the distribution layer 36 can be exposed and visible due to the lack of presence of the material of the absorbent core 34 at the absorbent core opening 44.

The absorbent core opening 44 can be located at various positions along the longitudinal and transverse directions of the absorbent core 34 depending upon the primary location of body exudate intake or the purpose for which the absorbent article 10 is being used. For example, in various embodiments, the absorbent core opening 44 can be positioned so that it is in substantial alignment with the longitudinal centerline 70 and the transverse centerline 72 of the absorbent article 10. This allows the opening to be centrally disposed so that it can be positioned below the main point of body exudate discharge and so that it can act as the primary body exudate receiving area for the absorbent article 10.

However, centralized positioning of the absorbent core opening 44 is not required, and in various embodiments, depending on the primary location where body exudate intake might occur, the absorbent core opening 44 may be substantially aligned with the longitudinal centerline 70 only. Thus, in various embodiments, the absorbent core opening 44 may be shifted in the longitudinal direction towards either transverse direction end edge, 12 or 14, of the absorbent article 10, so that the absorbent core opening 44 is not in substantial alignment with the transverse centerline 72.

The absorbent core opening 44 can have a longitudinal length from about 15, 20, 30 or 50 mm to about 60, 75, 100 or 145 mm and can have a transverse width from about 10, 15, 20 or 30 mm to about 40, 60 or 75 mm. The absorbent core opening 44 can have a longitudinal length that is from about 15, 20 or 25% to about 70, 75, or 80% of the overall longitudinal length of the absorbent core 34 in the longitudinal direction. The absorbent core opening 44 can have a transverse width that can be from about 20, 25 or 30% to about 70, 75 or 80% of the overall width of the absorbent core 34 in the transverse direction. The absorbent core opening 44 can serve to funnel and direct body exudates from the topsheet layer 20 and towards lower layers of the absorbent article 10 in the depth (Z) direction. The absorbent core opening 44 can also form a cup or well-like structure for holding body exudates and preventing its leakage away from a central region 90 of the absorbent article 10 and towards the edges of the absorbent article 10.

The absorbent core opening 44 can underlay the fluid transfer layer opening 40 in the absorbent article 10. The absorbent core opening 44 can have a longitudinal length and a transverse width that can be smaller in dimension than the longitudinal length and transverse width of the fluid intake layer opening 40. A portion of the body facing surface 62 of the absorbent core 34 can be visible to a user of the absorbent article 10.

Distribution Layer

The absorbent system can have a distribution layer 36 positioned below the absorbent core 34. The distribution layer 36 can increase absorbency of the absorbent article 10. The distribution layer 36 can be constructed of various materials such as, but not limited to, hydroentangled webs, through air bonded carded webs, meltblown webs, and meltblown microfiber webs. The distribution layer 36 can include a hydrophilic material. The distribution layer 36 can be larger in size than the absorbent system opening 50. The distribution layer 36 can be smaller in size than the absorbent core 34 of the absorbent article 10. The distribution layer 36 can be positioned within the absorbent article 10 such that the absorbent system opening 50 within the absorbent article 10 overlies the distribution layer 36.

At least a portion of the distribution layer 36 can be visible to the wearer of the absorbent article 10 through the absorbent system opening 50 in the absorbent article 10.

In various embodiments, the distribution layer 36 can have a longitudinal length from about 80, 90, 100, 110, 120, 125 or 130 mm to about 135, 140, 150, 160, 170, 180 or 190 mm and can have a transverse width from about 20, 30, 35 or 40 mm to about 45, 50, 55 or 60 mm. In various embodiments, the distribution layer can have a density of greater than about 0.1 grams per cubic centimeter. The density can be calculated utilizing the formula: density=basis weight (gsm)/thickness (mm)/1000. In various embodiments, the distribution layer 40 can have a basis weight from about 10, 20, 25, 30 or 50 gsm to about 60, 70, 80, 90, 100, 120, 140, 150, 160, 180 or 200 gsm.

In various embodiments, the distribution layer 36 can be a hydroentangled web. The hydroentangled web can include a hydroentangled spunbond material and a pulp material. The hydroentangled spunbond material can include a polypropylene material. The spunbond material can be present in an amount from about 10% or 15% to about 20% or 25% of the hydroentangled web. The pulp material can be present in an amount from about 75% or 80% to about 85%, 90% or 100% of the hydroentangled web. The hydroentangled web can have a basis weight from about 30 or 60 gsm to about 90, 200, or 300 gsm. Without being bound by theory, it is believed that a higher basis weight hydroentangled web can improve the absorbency of the distribution layer 36. It is further believed that an improved absorbency of the distribution layer 36 can further result in an improved fluid retention capacity of the absorbent article 10. The basis weight of the hydroentangled web can be balanced with the desired flexibility of the absorbent article 10. In various embodiments, the distribution layer 36 can be a pulp sheet material. In such embodiments, the distribution layer 36 can contain 100% pulp material. In such embodiments, the distribution layer 36 can have a basis weight from about 30 or 60 gsm to about 90, 200 or 300 gsm. In various embodiments, the distribution layer 36 can include a bicomponent fluid distribution layer, which can increase absorbency by providing a high void space and may be made of a through air bonded carded web, having a basis weight, in an embodiment, of between about 25 gsm and 100 gsm. In various embodiments, the distribution layer 36 can be a meltblown microfiber web of polypropylene material and can have a basis weight from about 10 or 20 gsm to about 30, 50 or 100 gsm. In various embodiments, the meltblown microfiber web can be treated with wetting agents for adequate handling of body exudates. Examples of wetting agents can include, but are not limited to, surface active agents (or surfactants) having a hydrophilic lipophilic balance (HLB) of at least 6, 7 or 18. A variety of surfactants can be used and can include, but are not limited to, anionic, cationic, or neutral from a charge standpoint. Mixtures of surfactants and other wetting agents can also be used. A wetting agent add-on can range from about 0.1 or 0.2% to about 5 or 10%. In various embodiments, an add-on amount can be higher than 10%. For example, the meltblown microfiber web can be treated to impart hydrophlicity by either Aerosol GPG of Cytec or Ahcovel Base N-62 for example. Such material is available from Yuhan-Kimberly Ltd., Seoul, Korea and FlberTex, Malaysia.

Backsheet Layer

The backsheet layer 22 is generally liquid impermeable and is the portion of the absorbent article 10 which faces the garment of the wearer. The backsheet layer 22 can permit the passage of air or vapor out of the absorbent article 10 while still blocking the passage of liquids. Any liquid impermeable material may generally be utilized to form the backsheet layer 22. The backsheet layer 22 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 22 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 22 can be a polyethylene film such as that obtainable from Pliant Corporation, Schaumburg, Ill., USA. Another example can include calcium carbonate-filled polypropylene film. In still another embodiment, the backsheet layer 22 can be a hydrophobic nonwoven material with water barrier properties such as a nonwoven laminate, an example of which can be a spunbond, meltblown, meltblown, spunbond, four-layered laminate. The backsheet layer 22 can, therefore, be of a single or multiple layer construction, such as of multiple film layers or laminates of film and nonwoven fibrous layers. Suitable backsheet layers 22 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Additional Layers

In various embodiments, an absorbent article 10 can optionally include at least one of a surge layer 64 and/or a shield layer 66. In various embodiments, an absorbent article 10 can include a surge layer or a shield layer. In various embodiments, an absorbent article 10 can include a shield layer and a surge layer.

Surge Layer

Figure 4:
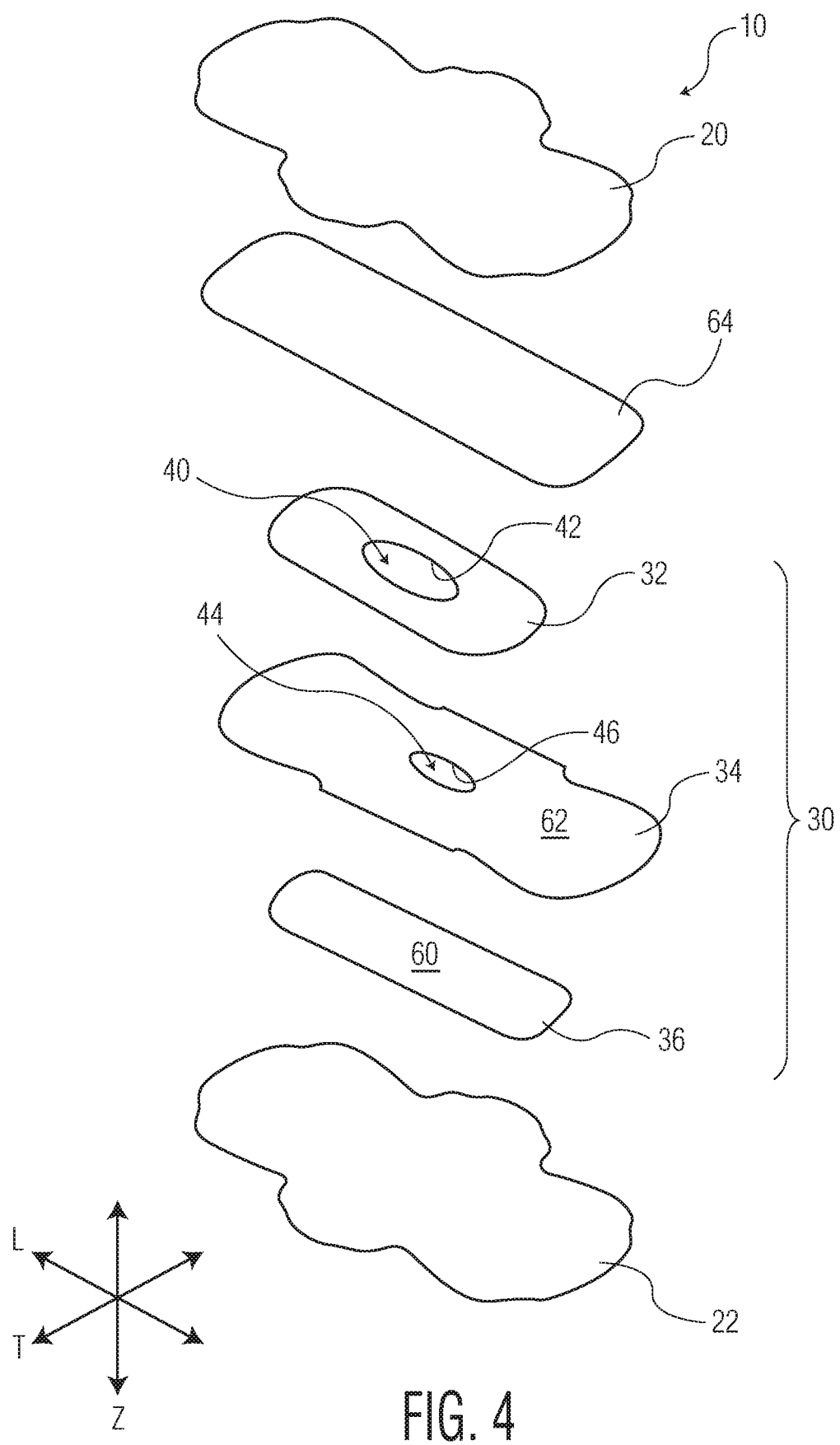
FIG. 4 is an exploded perspective view of an embodiment of an absorbent article.

An additional layer in the absorbent article 10 can be a surge layer 64, such as shown in FIG. 4. A surge layer 64 can be constructed of any woven or nonwoven material that is easily penetrated by body exudates. The surge layer 64 can help to absorb, decelerate, and diffuse surges or gushes of liquid that may be rapidly introduced into the absorbent article 10. The surge layer 64 can rapidly accept and temporarily hold the liquid prior to releasing the liquid into, for instance, the fluid intake layer 32 and/or absorbent core 34 or any other layer of the absorbent article 10. Various woven fabrics and nonwoven webs can be used to construct the surge layer 64. For example, the surge layer 64 can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layer 64 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layer 64 typically has a basis weight of less than about 100 gsm, and in some embodiments, from about 10 gsm to about 40 gsm.

The surge layer 64 can be incorporated into the absorbent article 10 in any suitable size and shape based upon the need of the particular absorbent article 10 in which the surge layer 64 is being used. In various embodiments, the surge layer 64 can extend across the entire absorbent article 10 in the longitudinal direction and transverse direction, such that the surge layer 64 can have the same dimensions as the topsheet layer 20. In various embodiments, the surge layer 64 can have a smaller overall length in the longitudinal direction and a smaller overall width in the transverse direction than the topsheet layer 20. In various embodiments, the overall length of the surge layer 64 can be from about 30, 40 or 50% to about 98, 99 or 100% of the overall length of the topsheet layer 20. In various embodiments, the overall width of the surge layer 64 can be from about 10, 25 or 50% to about 98, 99 or 100% of the overall width of the topsheet layer 20.

Shield Layer

Figure 5:
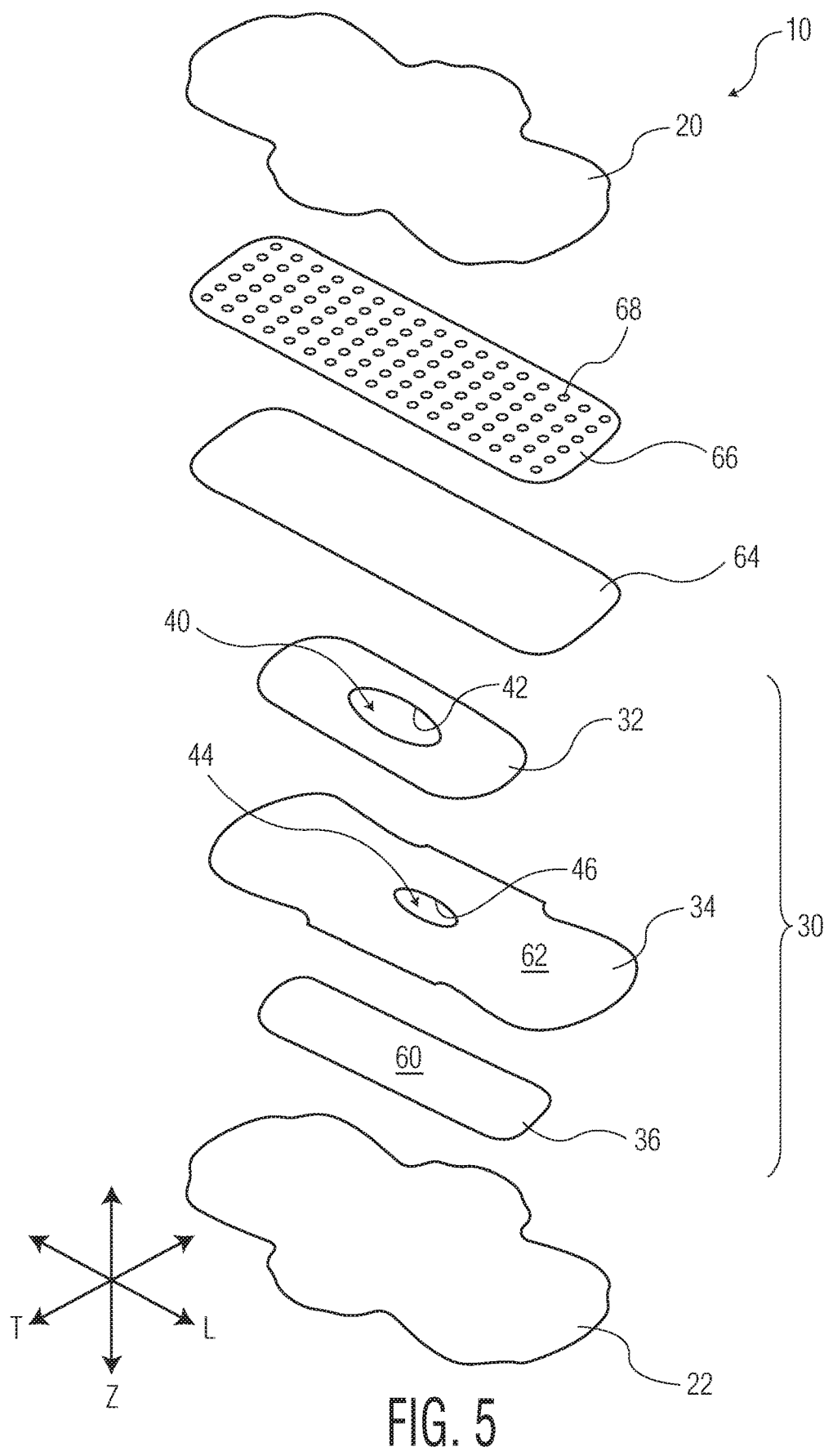
FIG. 5 is an exploded perspective view of an embodiment of an absorbent article.

Referring to FIG. 5, in various embodiments, the absorbent article 10 can include a shield layer 66. The shield layer 66 can be constructed of any suitable material such as, but not limited to, liquid permeable nonwoven materials, woven materials, films, etc. In various embodiments, the shield layer 66 can be constructed of a film material and can include any material which can be formed into a film including, but not limited to, polyolefins and polyacrylates, as well as copolymers and blends thereof. For example, polymers which can be utilized to form the film material can include, but are not limited to, polyethylene, low density polyethylene, linear low density polyethylene, polypropylene, polyvinyl chloride, polyvinyl alcohol, ethylene vinyl acetate, starch base resins, cellulose esters, polyurethanes, polycaprolactone, or combinations thereof. In various embodiments, the shield layer 66 can be constructed of a film material which can be a three-dimensional, aperture film made of polyethylene. For instance, the film material can be a perforated film having apertures 68 which can be tapered capillaries. The apertures 68 in the film material can function to draw body exudates away from the skin of the wearer of the absorbent article 10. In various embodiments, the apertures 68 in the shield layer 66 can be localized to a portion of the shield layer 66. In various embodiments, the apertures 68 in the shield layer 66 can extend across the entire surface of the shield layer 66, such as illustrated in FIG. 5. The number and size of the apertures 68 can be controlled such that the shield layer 66 can have a percent aperture area due to the presence of the apertures 68 of from about 10, 15 or 20% to about 40, 60 or 80%. The shield layer 66 can be imparted with apertures 68 which can have any shape as deemed suitable, such as, for example, hexagonal, circular, ovular, elliptical, polygonal, or any other suitable pattern or combination of shapes. Each aperture 68 can have an average diameter of from about 50, 100, or 200 microns to about 800, 1000, or 1500 microns, where the diameter is large enough to allow body exudates to be acquired through the shield layer 66 as rapidly as the body exudates are delivered.

The shield layer 66 can be incorporated into the absorbent article 10 in any suitable size and shape based upon the need of the particular absorbent article 10 in which the shield layer 66 is being used. In various embodiments, the shield layer 66 can extend across the entire absorbent article 10 in the longitudinal direction and transverse direction, such that the shield layer 66 can have the same dimensions as the topsheet layer 20. In various embodiments, the shield layer 66 can have a smaller overall length in the longitudinal direction and a smaller overall width in the transverse direction than the topsheet layer 20. In various embodiments, the overall length of the shield layer 66 can be from about 30, 40 or 50% to about 98, 99 or 100% of the overall length of the topsheet layer 20. In various embodiments, the overall width of the shield layer 66 can be from about 10, 25 or 50% to about 98, 99 or 100% of the overall width of the topsheet layer 20.

Embossing

In various embodiments, the absorbent article 10 can have one or more embossed regions formed in one or more layers of the absorbent article 10. Generally, the embossed regions can be described as channels formed in the absorbent article 10 due to deformations of the layer(s) of the absorbent article 10. The embossed regions are formed in any suitable pattern to not only create an aesthetically pleasing surface, but also to facilitate funneling of body exudates towards a desired location in the absorbent article 10. The embossed regions may also improve the consistency of the fit properties of the absorbent article 10, both before and after receiving body exudates. The embossed regions may be provided in either a symmetric or asymmetric manner to the absorbent article 10.

Further, the embossed regions can be formed using any known conventional technique known in the art. Suitable techniques includes, for example, the use of raised elements to impart the desired embossing pattern to create compressed channels in the layer(s) of the absorbent article 10. For instance, a suitable process may include using thermal bonding wherein the absorbent article 10 is passed through two rolls (e.g., steel, rubber, etc.) where one is engraved with an embossing pattern and the other is flat. One or both rolls may be heated. In addition, thermal and/or ultrasonic bonding techniques may be employed to create the embossing regions.

The absorbent article 10 can have at least one embossed region 80. The embossed region 80 can provide both an aesthetically pleasing appearance and topography to the absorbent article 10 which can direct body exudates to a desired location and prevent leakage and/or pooling of the body exudate around the edge of the absorbent article 10.

In various embodiments, the embossed region 80 can generally extend around the entire absorbent article 10 in a generally oblong shape. In various embodiments, the embossed region 80 can have a protrusion(s) in the longitudinal and/or transverse directions of the absorbent article 10 to provide any additional desired shaping to the embossed region 80. The embossed region 80 can generally surround and frame the fluid intake layer 32 and the distribution layer 36 of the absorbent article 10. In various embodiments, the embossed region 80 surrounds the fluid intake layer 32 and the distribution layer 36 without penetrating into the fluid intake layer 32 or the distribution layer 36. In various embodiments, a distance separating the fluid intake layer 32 and the distribution layer 36 from an embossed region 80 can be from about 1, 1.5, 2, 2.5, or 3 mm to about 3.5, 4, 4.5, 5, or 5.5 mm. The size and shape of the fluid intake layer 32 and the distribution layer 36 can be varied respectively inside the embossed region 80. FIG. 1 provides an exemplary illustration of an embossed region 80 in which the embossed region 80 has an opposing pair of longitudinally extending side portions 80a which extend the longitudinal length of the absorbent article 10. The embossed region 80 also has an opposing pair of transversely extending end portions 80b which are present in proximity to the transverse end edges, 12 and 14, of the absorbent article 10 and which connect the longitudinally extending side portions 80a. While the embossed region 80 is illustrated as extending the majority of the absorbent article 10 longitudinal length, it is to be understood that the embossed region 80 can be any size and shape as desired and can be located in only the central region 90 of the absorbent article 10 or can extend into either or both end region, 92 and/or 94, of the absorbent article 10.

In various embodiments, the absorbent article 10 can have one or more second embossed regions 82. A second embossed region 82 can be positioned in either or both end region, 92 and/or 94, of the absorbent article 10. In various embodiments in which an embossed region 80 extends generally the majority of the longitudinal length of the absorbent article 10, the one or more second embossed regions 82 can be positioned in closer proximity to the fluid intake layer 32 in either or both end regions, 92 and/or 94, of the absorbent article 10. In the exemplary illustration of FIG. 1, the second embossed regions can have a semi-circular shape, although any other suitable shape can be used. The second embossed regions 82 can be formed through any of the layers of the absorbent article 10 without penetrating into the fluid intake layer 32. In various embodiments in which the absorbent article 10 has an embossed region 80 and at least one second embossed region 82, the combination of the embossed region 80 and the second embossed region 82 can surround and frame the fluid intake layer 32 of the absorbent article 10.

Wings

The wings 26 can be constructed from materials described above with respect to the topsheet layer 20 and the backsheet layer 22. In various embodiments, the wings 26 can comprise an extension of a layer of material within the topsheet layer 20 and/or the backsheet layer 22. By way of example, the wings 26 can be formed by an extension of the topsheet layer 20 and backsheet layer 22 that are then bonded together along peripheral seal 24. Such wings 26 can be integrally formed with the main portion of the absorbent article 10. Alternatively, the wings 26 can be formed independently and separately attached to an intermediate section of the absorbent article 10. Wings 26 that are made independent of the other components of the absorbent article 10 can be bonded to a portion of the topsheet layer 20 and/or backsheet layer 22. Examples of processes for manufacturing absorbent articles 10 and wings 26 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a longitudinal direction, a transverse direction, and a depth direction;
   b. a topsheet layer and a backsheet layer; and
   c. an absorbent system positioned between the topsheet layer and the backsheet layer, the absorbent system comprising:
      i. a fluid intake layer positioned below the topsheet layer in the depth direction of the absorbent article;
      ii. an absorbent core positioned below the fluid intake layer in the depth direction of the absorbent article; and
      iii. a distribution layer positioned below the absorbent core in the depth direction of the absorbent article and capable of distributing fluid in at least the longitudinal direction of the absorbent article;
   wherein the fluid intake layer defines a fluid intake layer opening having a first longitudinal length and a first transverse width and the absorbent core defines an absorbent core opening having a second longitudinal length and a second transverse width wherein the second longitudinal length and the second transverse width of the absorbent core opening is smaller than the first longitudinal length and first transverse width of the fluid intake layer opening and wherein a spatial gap exists between the topsheet layer and the distribution layer and wherein the distribution layer is a hydroentangled web comprising from about 10-25% of a spunbond material and from about 75-90% of a pulp material.

2. The absorbent article of claim 1 wherein the distribution layer comprises a hydrophilic material.

3. The absorbent article of claim 1 wherein the distribution layer has a density greater than 0.1 grams.

4. The absorbent article of claim 1 wherein the distribution layer has a basis weight from about 10 gsm to about 300 gsm.

5. The absorbent article of claim 1 wherein the distribution layer has a longitudinal length from about 80 mm to about 190 mm.

6. The absorbent article of claim 1 wherein the distribution layer has a transverse width from about 20 mm to about 60 mm.

7. The absorbent article of claim 1 wherein the fluid intake layer opening has a longitudinal length from about 15 mm to about 150 mm.

8. The absorbent article of claim 1 wherein the fluid intake layer opening has a transverse width from about 10 mm to about 80 mm.

9. The absorbent article of claim 1 wherein a height of the spatial gap from the topsheet layer to the distribution layer is from about 1 mm to about 8 mm.

10. The absorbent article of claim 1 further comprising a shield layer.

11. The absorbent article of claim 10 wherein the shield layer comprises an aperture film material.

12. The absorbent article of claim 1 further comprising a surge layer.

* * * * *